United States Patent [19]

Ruano

[11] Patent Number: 4,955,860

[45] Date of Patent: Sep. 11, 1990

[54] VOLUMETRIC PUMP FOR PARENTERAL PERFUSION

[76] Inventor: Miguel M. Ruano, c/o Dr. Moliner No. 2-10, Valencia, Spain, 46010

[21] Appl. No.: 180,067

[22] Filed: Apr. 11, 1988

[30] Foreign Application Priority Data

Apr. 9, 1987 [ES] Spain .................................. 8701025

[51] Int. Cl.[5] .............................................. A61M 5/00
[52] U.S. Cl. ...................................... 604/67; 604/141; 128/DIG. 12
[58] Field of Search ................... 604/65, 67, 140, 141, 604/143, 147, 151, 153; 128/DIG. 12, DIG. 13

[56] References Cited

U.S. PATENT DOCUMENTS

| | | |
|---|---|---|
| 3,640,277 | 2/1972 | Adelberg ............................ 604/141 |
| 3,756,459 | 9/1973 | Bannister et al. ................... 604/141 |
| 3,895,741 | 7/1975 | Nugent ............................... 604/141 |
| 4,539,005 | 9/1985 | Greenblatt ........................... 604/141 |
| 4,626,243 | 12/1986 | Singh et al. ........................ 604/141 |
| 4,657,160 | 4/1987 | Woods et al. ....................... 604/141 |
| 4,684,367 | 8/1987 | Schaffer et al. ..................... 604/141 |
| 4,714,462 | 12/1987 | DiDomenico ....................... 604/141 |
| 4,735,613 | 4/1988 | Bellin et al. ........................ 604/141 |
| 4,778,451 | 10/1988 | Kamen ................................. 604/67 |

*Primary Examiner*—Stephen C. Pellegrino
*Assistant Examiner*—Ralph Lewis
*Attorney, Agent, or Firm*—Fleit, Jacobson, Cohn, Price, Holman & Stern

[57] ABSTRACT

Volumetric pump for use in the parenteral perfusion of solutions without the need for the substitution or inclusion of additional elements in traditionally used dropper systems. The pump consists of a rigid chamber (1) containing a bag (2) with the solution to be perfused and is set up in a common volume formed by a liquid or gaseous interface with another chamber (3) to which it is connected, acting as a pump or pumping agent, and equipped with a distendable membrane (4), which acts on the walls of the bag (2), extracting the residual air by means of suction through the duct (8) which has a valve (5). The solution then passes through a connection tube (6) and is perfused. There is a stopcock (7) in the passage connecting the compartments (1) and (3), and the system is equipped with timers (9) which enable the selected flow to be determined and a servomechanism (10) to ensure greater precision.

3 Claims, 1 Drawing Sheet

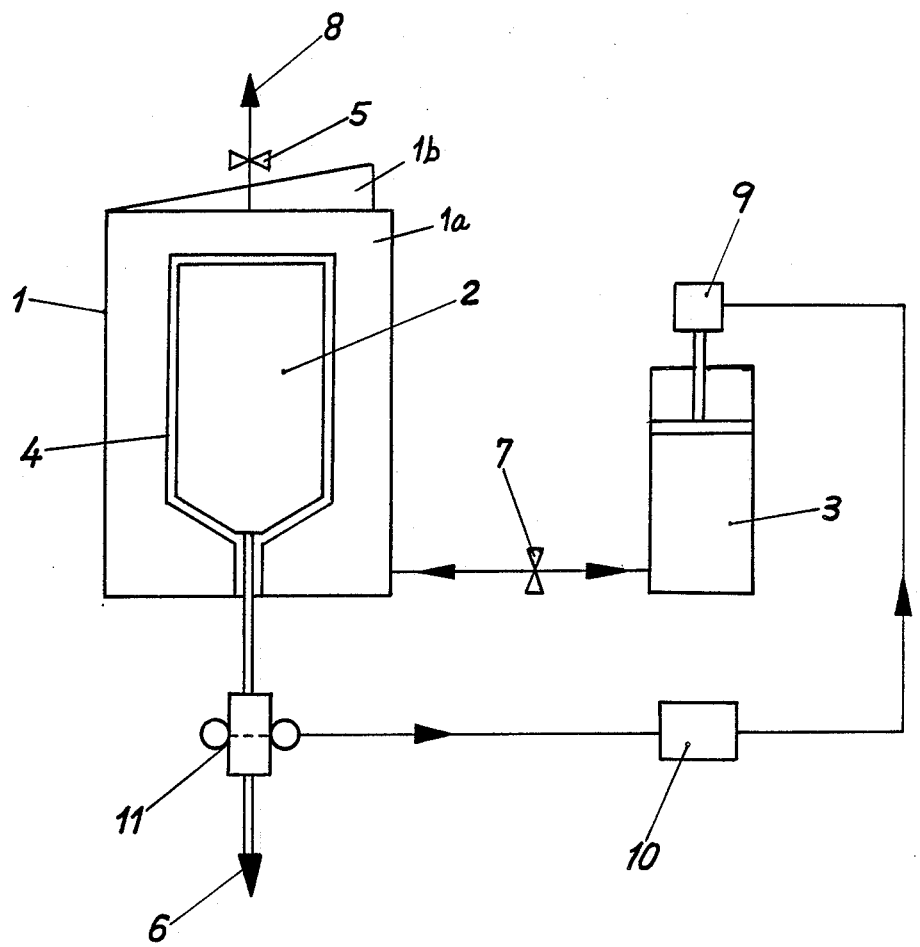

VOLUMETRIC PUMP FOR PARENTERAL PERFUSION

BACKGROUND OF THE INVENTION

This invention relates to a volumetric pump for the parenteral perfusion of solutions, without the need for the substitution or inclusion of additional elements in traditionally used dropper systems.

In the evolution of hospital medicine over the last twenty years, there has been an extraordinary increase in the use of solutions for parenteral administration. The traditional systems used, consisting of dropper chambers and flow regulation by means of metal plates or wheels which narrowed the diameter of the tube, are extremely unsatisfactory with regard to precision, constancy and range of flows. They lack mechanisms to detect cases in which the dropping operation has terminated or the system is blocked, and other defects in the system. In order to solve these problems which are especially important in the administering of intravenous drugs, various models of infusion pumps have appeared on the market, which control the flows by means of different systems: peristaltic, syringes, chambers with compressible rings, etc. All these pumps made it necessary to substitute or include additional elements in the traditional lines, and for reasons of infectious prophylaxis, these elements had to be changed every 24 hours in the case of each patient.

BRIEF SUMMARY OF THE INVENTION

Taking into consideration that one of the most widely used forms of solutions for parenteral administration is available in collapsable bags, thus enabling a system to be developed which acts directly on the bag containing the flow for intravascular administration and achieves the volumetric control of the perfusion, without the need for including other elements to the traditional system, a study was made on the inclusion of the volumetric pump mentioned above, in order to ensure complete safety and optimum working conditions in its operation.

The system consists basically of a rigid chamber containing a hermetic bag with the solution to be perfused. By means of a liquid or gaseous interface, a common volume with a separate chamber is established to which it is connected, which will act as a pump or pumping agent.

The operation consists of setting up a liquid interface without establishing direct contact with the bag containing the solution, so that a rigid chamber is formed which maintains the fluid in a water-tight compartment by means of a membrane that can be distended and acts directly on the outer walls of the bag containing the solution to be perfused. The chamber can be opened out into two parts like a book. On the inner walls is the membrane on which the perfusion bag is to be placed. Having done this, the chamber is hermetically sealed and any residual air extracted by suction applied through a duct for this purpose, equipped with a valve guaranteeing watertightness.

After proceeding as outlined above, the solution to be perfused and the pumping fluid are separated by the walls of the bag and the chamber membrane, which make up practically the whole of the volume in the rigid chamber. As a result, any changes in volume that penetrate the pump cavity will be transmitted immediately in a linear manner to the outer chamber and therefore the solution to be perfused will leave the pump at an equivalent volume through the tube connected to the patient.

There are many variations which make it possible to apply the same principle of operation as the one we are describing here, such as for example, placing the bag containing the solution to be perfused in direct contact with the pumping fluid without the separating membrane. In the area connecting both compartments of the rigid chamber and the pressure chamber, there is a stopcock. When the bag is placed inside the rigid chamber compartment and it has been sealed, the tube connecting it to the pressure chamber opens to let the solution through, and the air escapes through a duct made for this purpose in the upper part.

The perfusion flow is controlled by a pump which in turn can be activated by any mechanism, a piston or a syringe, a peristaltic device, a container with a compressible ring, etc. All these are equipped with timers to determine the selected flow.

Any one of the variations may include a servomechanism, in order to ensure greater precision. By counting the drops of solution in the chamber in the patient, this device is able to establish the volume actually administered. This information can be used to regulate the operation of the pump, thus correcting possible deviations in the established flow.

The system we are referring to here will include the alarm and control mechanisms usually found in intravascular perfusion pumps, for cases when the system becomes blocked or when there are air bubbles in the perfusion line, etc. and unlike the existing systems, allows for the solution administered to be controlled without having to substitute elements or act on the traditional dropper line or system.

Basically, the volumetric pump for parenteral perfusion of solutions without the need for the substitution or inclusion of additional elements in traditional dropper systems described herein enables the administering of the perfusion solution through compression of the bag containing the solution, by means of a pump or similar device which controls the flow and volume to be administered as desired.

The volumetric pump system for use in parenteral perfusion described above is different from other systems in that it enables the solution administered to be controlled without having to substitute new elements or otherwise act on traditional dropper systems, and this modified system acts as a pumping chamber. In this manner the system described above is the only one which uses the action of the pump on the bag containing the solution to be perfused, not by means of a simple application of pressure, but by controlling the flow and volume to be administered as desired.

BRIEF DESCRIPTION OF THE DRAWING

In order to gain a better understanding of the general characteristics mentioned above, a detailed description follows with a sheet which shows graphically a case in which the volumetric pump for parenteral perfusion mentioned in this description was actually used. It should be said that in view of the predominantly informative nature of the drawing, the FIGURE drawn should be examined using the widest criteria and by no means should it be considered restrictive.

The single FIGURE shown in the accompanying drawing is a general schematic view of all the components of the system, the interconnecting elements between them and their operation.

DETAILED DESCRIPTION

Referring to the drawing, numerical notes have been included which are related to the descriptions of the characteristics and operation that are listed below. In this way, they can immediately be found. They consist mainly of a rigid chamber (1) containing a bag (2) with the solution to be perfused. A common volume is formed by a liquid or gaseous interface between the chamber (1) and another chamber (3) with which it is connected, and the chamber (3) acts as a pump or agent that pumps the fluid.

Basically the system consists of the creation of a liquid interface without establishing direct contact with the bag (2) containing the solution, and the rigid chamber (1) maintains the solution in a watertight compartment by means of a separating distendable membrane (4) which acts directly on the walls of the bag (2) containing the solution to be perfused.

The chamber (1) can be opened up into two halves 1a and 1b like a book; the membrane (4) on which the perfusion bag will be placed (2) is located on its inner walls and the chamber (1) is hermetically sealed immediately afterwards. Then any residual air is suctioned out through the duct (8) which is equipped with a valve (5) ensuring it is watertight.

From this time on, the solution to be perfused and the pumping fluid separated by the walls of the bag (2) and the membrane (4) in the rigid chamber (1) will make up practically the whole of the volume of the rigid chamber itself; as a result, any changes in volume penetrating the pump (3) cavity will be transmitted immediately in a linear manner to the chamber (1), and therefore to the solution to be perfused which will pass through the tube (6) connected to the patient at an equivalent volume.

In the passage connecting both compartments (1) and (3) there is a stopcock (7). In this way, once the bag (2) is placed inside the compartment (1) which has been sealed, the passage connecting both compartments (1) and (3) opens up to let the pumping fluid through, and the air leaves through the duct for this purpose (8) located at the upper part. There are many variations possible in the application of this same principle of operation, such as for example placing the bag (2) containing the solution in direct contact with the pumping fluid, without a separating chamber.

The perfusion rate will be controlled by the pump (3) which can be activated by any mechanism, a piston or a syringe, as can be seen in the attached drawing, through peristalsis, a container with a compressible ring or any other type, all equipped with the corresponding timers (9) to determine the selected flow.

Any of the methods used may include a servomechanism (10) to guarantee greater precision which by counting of the drops of fluid in the chamber (11) in the patient can establish the volume actually administered to him. This information can then be used to regulate the pump (3) operation, correcting any deviations in the preselected flow.

Considering that we have described in sufficient detail each and every one of the parts making up this volumetric pump for parenteral perfusion, it only remains for us to mention the possibility of the different parts being constructed in a variety of materials, shapes and sizes, and any modifications required for practical purposes can be incorporated, provided that these do not alter the essential points of this device, presented here for inclusion in the Patents Register.

I claim:

1. Apparatus for parenteral perfusion of a liquid to a patient from a perfusion bag having an outlet tube, said apparatus comprising a rigid housing defining an interior chamber for receiving a perfusion bag in a gas-tight manner, a perfusion bag within said chamber so that said chamber defines an enclosed space surrounding said bag, said bag having an outlet tube extending from said chamber, suction means for evacuating said space, a volumetric fluid pump, connection means between said pump and said housing for filling said space with pressurized fluid received from said pump for applying pressure on said bag to produce perfusion of liquid in said bag through said tube, means for controlling the rate of fluid flow from said pump into said space to control the perfusion rate, and sensor means for sensing the amount of liquid administered to the patient through the outlet tube and operatively connected to said means for controlling the rate of fluid flow from said pump into said space.

2. Apparatus as claimed in claim 1 wherein said housing includes a membrane within said chamber and surrounding said bag, said membrane defining an inner wall in said space.

3. Apparatus as claimed in claim 1 wherein said housing comprises two halves which can be opened like a book for insertion of said bag in said space between said two halves.

* * * * *